(12) United States Patent
Yamagata et al.

(10) Patent No.: US 6,429,296 B2
(45) Date of Patent: *Aug. 6, 2002

(54) COMPLEX OF HUMAN GROWTH HORMONE AND ZINC AND USE

(75) Inventors: Yutaka Yamagata, Kobe; Masafumi Misaki, Takarazuka; Susumu Iwasa, Kyotanabe, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/767,144

(22) Filed: Jan. 23, 2001

Related U.S. Application Data

(62) Division of application No. 09/151,783, filed on Sep. 11, 1998, now Pat. No. 6,191,107.

(30) Foreign Application Priority Data

Sep. 26, 1997 (JP) .............................................. 9-261251

(51) Int. Cl.⁷ ........................ A61K 38/27; A61K 33/30; A01N 59/16
(52) U.S. Cl. ...................... 530/399; 530/399; 530/839; 514/12; 514/21; 424/423; 424/426; 424/502; 424/489; 424/494; 424/641; 424/78.31; 424/78.34
(58) Field of Search ................................ 424/423, 426, 424/502, 484, 494, 500, 85.1, 78.31, 78.34; 514/12, 21; 530/399, 839

(56) References Cited

U.S. PATENT DOCUMENTS

| | | | |
|---|---|---|---|
| 5,654,010 A | * | 8/1997 | Johnson ...................... 424/502 |
| 6,191,107 B1 | * | 2/2001 | Yamagata ...................... 514/12 |

FOREIGN PATENT DOCUMENTS

| | | |
|---|---|---|
| EP | 0 216 485 | 4/1987 |
| EP | 0 633 020 A1 | 1/1995 |
| WO | 92/17200 | 10/1992 |
| WO | 94/12158 | 6/1994 |
| WO | 95/29664 | 11/1995 |
| WO | 96/07399 | 3/1996 |
| WO | WO92/17200 | 10/1996 |
| WO | 96/40072 | 12/1996 |
| WO | WO96/40074 | 12/1996 |
| WO | 97/01331 | 1/1997 |
| WO | WO97/03692 | 2/1997 |
| WO | 98/27980 | 7/1998 |

OTHER PUBLICATIONS

O. L. Johnson et al., "A month–long effect from a single injection of microencapsulated human growth hormone", Nature Medicine, vol. 2, No. 7, pp. 795–799, Jul. 1996.

R. B. Aisina et al., "Microencapsulation of somatotropic growth hormone", S.T.P. Pharma Sciences, vol. 4, No. 6, pp. 437–441, 1994.

H. Lee et al., "*In vivo* Characterization of Sustained–Release Formulations of Human Growth Hormone", The Journal of Pharmacology and Experimental Therapeutics, vol. 281, No. 3, pp. 1431–1439, 1997.

* cited by examiner

*Primary Examiner*—Christopher S. F. Low
*Assistant Examiner*—Chih-Min Kam
(74) *Attorney, Agent, or Firm*—Wenderoth, Lind & Ponack, L.L.P.

(57) ABSTRACT

The present invention provides a complex of human growth hormone and zinc containing human growth hormone and zinc at a molar ratio of about 1:1.6 to about 1:2.4, and a sustained-release preparation which comprises the complex of human growth hormone and zinc and a biodegradable polymer and which has a high entrapment ratio of human growth hormone and exhibits a stable sustained-release suppressing the initial burst.

7 Claims, 1 Drawing Sheet

COMPLEX OF HUMAN GROWTH HORMONE AND ZINC AND USE

This application is a division of Ser. No. 09/151,783, filed Sep. 11, 1998 now U.S. Pat. No. 6,191,107, which claims the benefit of foreign priority under 35 U.S.C.§119 (a)–(d) from Japan Application No. 261251/1997, filed Sep. 26,1997.

The present invention relates to a complex of human growth hormone and zinc containing human growth hormone and zinc at a molar ratio of about 1:1.6 to about 1:2.4, a sustained-release preparation which comprises the complex of human growth hormone and zinc and a biodegradable polymer, and so on.

BACKGROUND ART

In recent years, human growth hormone (hereinafter abbreviated as GH) has been produced on a large scale by utilizing genetic engineering technology, and is used widely, for example, being clinically applied to Turner's syndrome, infantile chronic renal diseases, achondroplasia and adult GH hyposecretion as well as pituitary dwarfism. Further, applications for osteoporosis in an aging society and static heart diseases are expected.

Since GH is usually administered by intramuscular or subcutaneous injection repeatedly and over a long term, due to consideration of stability in the body, a significant physical burden on patients is a problem. For instance, in the case of pituitary dwarfism, a daily subcutaneous administration to infants or young patients over a long period of time ranging from a few months to at least 10 years is practiced. On the one hand, development of a sustained-release preparation containing GH, which is medicinally effective with an administration ranging from once every few weeks to few months, has been reported (S.T.P. Pharma. Sci., 4(6), pages 437–441, 1994; Nature Med., 2(7), pages 795–799, 1996; J.Pharm.Exp.Ther., 281, pages 1431–1439, 1997,; WO 94/12158; WO 95/29664; WO 97/01331).

DETAILED DESCRIPTION OF INVENTION

Figure 1:
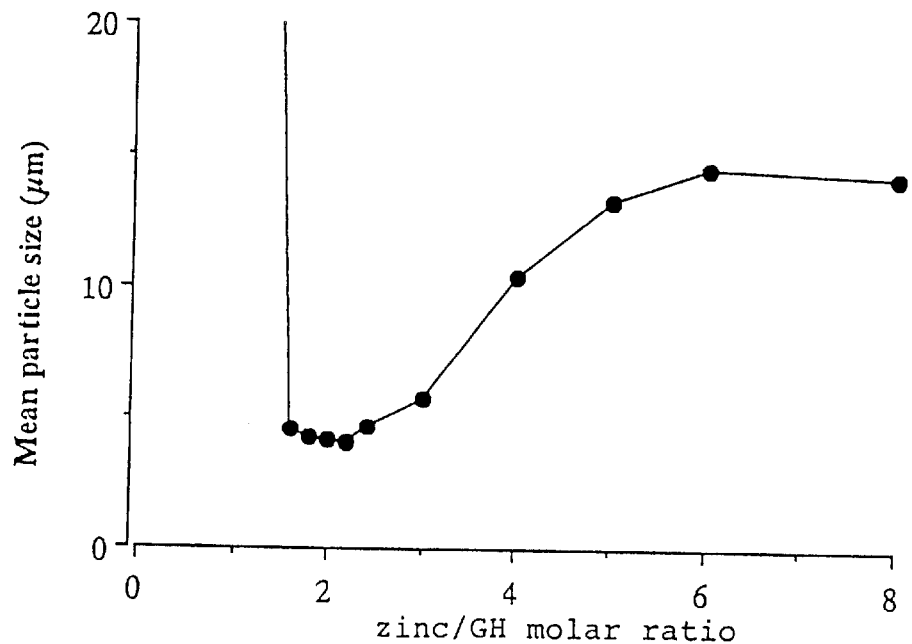
FIG. 1 shows the changes in particle size distribution according to the changes in the composition ratio of GH and zinc in a complex of GH and zinc.

Current sustained-release preparations containing GH have been produced by a method which comprises making GH in water (in water phase) and dispersing the water phase in organic solvent (in oil phase) containing a biodegradable polymer to make a water-in-oil emulsion. But, in this method, GH is remarkably denaturalized in the production process or on the shelves and a sufficient entrapment ratio and release is not obtained. On the one hand, a method which comprises dispersing GH powder into organic solvent (in oil phase) containing a biodegradable polymer to make a solid-in-oil dispersion is not appropriate for producing a sustained-release preparation on a large scale, since it is necessary to maintain stability by spraying the solid-in-oil dispersion into liquid nitrogen. Furthermore, since GH is not in the form of fine particles and is usually used after atomizing, the activity of GH is remarkably lowered by atomization of GH and it is difficult to make a solid-in-oil dispersion containing GH having at a high content.

Thus, it is very difficult to maintain stability of GH and micronize GH in the process for producing preparations. Further, it is very difficult to produce quality sustained-release preparations containing a high content of GH on a large-scale without lowering the activity of GH but at the same time maintaining quality and stability.

Therefore, a clinically useful preparation comprising GH which overcomes the above problems and has constant release over a long period of time, and a method for producing the sustained-release preparation on a large scale at high yield, are desired.

The present inventors made extensive and intensive studies and as a result, made a complex of GH and zinc containing GH and zinc at a molar ratio of about 1:1.6 to about 1:2.4 for the first time. Further, they found that the complex is substantially water-soluble and the micronization of the complex is easier than GH itself, without lowering the activity of GH, and when the obtained complex of GH and zinc having a small particle diameter is used to produce a sustained-release preparation, the sustained-release preparation can be produced on a large scale with assured stability and without denaturalizing GH in the process, having also an enhanced entrapment of GH and an improvement in release properties.

Namely, the present invention provides (1) a complex of human growth hormone and zinc containing human growth hormone and zinc at a molar ratio of about 1:1.6 to about 1:2.4, (2) a complex of the above (1), which is water-soluble, (3) a complex of the above (1), wherein the mean particle diameter of the complex is less than about 10 $\mu$m, (4) a sustained-release preparation, which comprises the complex of the above (1) and a biodegradable polymer, (5) a preparation of the above (4), wherein the biodegradable polymer is an aliphatic polyester, (6) a preparation of the above (5), wherein the aliphatic polyester is a polymer of lactic acid and glycolic acid, (7) a preparation of the above (6), wherein the content ratio of a polymer of lactic acid and glycolic acid is 100/0 to 40/60 (mole %), (8) a preparation of the above (5), wherein the weight-average molecular weight of the aliphatic polyester is about 3,000 to about 20,000, (9) a preparation of the above (5), wherein the aliphatic polyester is a salt of polyvalent metal,

(10) a preparation of the above (9), wherein the polyvalent metal is zinc,

(11) a preparation of the above (4), wherein the preparation is a microcapsule,

(12) a preparation of the above (11), wherein the microcapsule is for injection,

(13) a preparation of the above (4), wherein the initial burst ratio of GH is less than about 50%,

(14) a method for producing a complex of human growth hormone and zinc, which comprises mixing human growth hormone and zinc salt at a molar ratio of about 1:1.6 to about 1:2.4,

(15) a method for producing micronized human growth hormone, which comprises forming a complex of human growth hormone and zinc containing human growth hormone and zinc at a molar ratio of about 1:1.6 to about 1:2.4 and atomizing them,

(16) use of a complex of human growth hormone and zinc containing human growth hormone and zinc at a molar ratio 4 of about 1:1.6 to about 1:2.4 for producing a sustained-release preparation containing human growth hormone,

(17) a method for producing a sustained-release preparation containing human growth hormone, which comprises dispersing a complex of human growth hormone and zinc containing human growth hormone and zinc at a molar ratio of about 1:1.6 to about 1:2.4 in an oil phase containing a biodegradable polymer to make a solid-in-oil emulsion, adding the solid-in-oil emulsion to water phase to make a solid-in-oil-in-water emulsion, and then in-water drying the solid-in-oil-in-water emulsion,

(18) a pharmaceutical composition which comprises the complex of the above (1), and

(19) a pharmaceutical composition for treating or preventing pituitary drawfism, which comprises the complex of the above (1).

GH used in the present invention may be any type, for example, natural type (extracted products, etc.) or genetic recombinant type GH (Nature Vol.281, page 544 (1979), Vol.293, page 408 (1981), Proc. Natl. Acad. Sci. USA, Vol.80, page 397(1983), Biotechnol., Vol.5, page 161(1981), etc.), and genetic recombinant type GH is preferred in terms of its safety and quality. Further, in the present invention, muteins, derivatives, analogous and active fragments of GH may be used as GH (J.Biol.Chem., Vol.253, page 2679 (1978), B.B.R.C., Vol.92, page 511 (1980), Endocrinol., Vol.109, page 1301(1981), Protein Eng. Vol.3, page 49(1989), etc.).

Complexes of GH and zinc according to the present invention may be produced by any method, for example, methods generally used in the production of complexes, suitable for a molar ratio of GH and zinc in the range of from about 1:1.6 to about 1:2.4. The said complex of GH and zinc is usually produced by bringing GH into contact with a water-soluble zinc salt. This contact reaction is preferably employed in a solvent, for example, aqueous-solvent. The reaction time ranges from 1 minute to 1 hour. The reaction temperature ranges from 4° C. to 37° C. Water-soluble zinc salts used in this method, include salts of zinc and inorganic acids, salts of zinc and organic acids and so on. Inorganic acids include hydrochloric acid, sulfuric acid, nitric acid, thiocyanic acid and so on and organic acids include aliphatic carboxylic acids, aromatic acids and so on.

Examples of aliphatic carboxylic acids used as organic acids, are aliphatic monocarboxylic acids, aliphatic dicarboxylic acids, and aliphatic tricarboxylic acids. These aliphatic carboxylic acids may be saturated or unsaturated. The aliphatic carboxylic acid is preferably an aliphatic carboxylic acid having 2 to 9 carbon atoms.

Examples of aliphatic monocarboxylic acids are saturated aliphatic monocarboxylic acids having 2 to 9 carbon atoms (e.g., acetic acid, propionic acid, butyric acid, valeric acid, caproic acid, enanthic acid, caprylic acid, pelargonic acid, caprynic acid etc.) and unsaturated aliphatic monocarboxylic acids having 2 to 9 carbon atoms (e.g., acrylic acid, propiolic acid, methacrylic acid, crotonic acid, isocrotonic acid etc.).

Examples of aliphatic dicarboxylic acids are saturated aliphatic dicarboxylic acids having 2 to 9 carbon atoms (e.g., malonic acid, succinic acid, glutaric acid, adipic acid, pimelic acid etc.) and unsaturated aliphatic dicarboxylic acids having 2 to 9 carbon atoms (e.g., maleic acid, fumaric acid, citraconic acid, mesaconic acid etc.).

Examples of aliphatic tricarboxylic acids are saturated aliphatic tricarboxylic acids having 2 to 9 carbon atoms (e.g., tricarballylic acid, 1,2,3-butanetricarboxylic acid etc.).

The above-mentioned aliphatic carboxylic acids may have 1 or 2 hydroxyl groups. Such aliphatic carboxylic acids include glycolic acid, lactic acid, glyceric acid, tartronic acid, malic acid, tartaric acid, citric acid and so on.

The aliphatic carboxylic acid is preferably an aliphatic monocarboxylic acid, more preferably an aliphatic monocarboxylic acid having 2 to 9 carbon atoms, and still more preferably a saturated aliphatic monocarboxylic acid having 2 or 3 carbon atoms. Examples of particularly preferable aliphatic carboxylic acids include acetic acid and so on.

Examples of aromatic carboxylic acids used as the above-organic acid are benzoic acid and salicylic acid, with preference given to benzoic acid.

For example, a complex of GH and zinc in the present invention is produced by mixing GH and a water-soluble zinc salt at a mixing ratio (molar ratio) of about 1:1.6 to about 1:2.4, preferably about 1:1.8 to about 1:2.2 in a aqueous solvent (e.g., aqueous solutions containing ethanol, acetonitril or acetone at a concentration (for example, about 1 to about 10%(W/W)) which does not exert an adverse influence on the solubility of GH and a water-soluble zinc salt, preferably water). The said complex may be a compound (complex salt, double salt, salt, and organic metal compound etc.) formed by intermolecular binding between GH and zinc or a mixture of compounds which differ in their binding patterns. The composition ratio (molar ratio) of GH and zinc in the complex of GH and in the present invention is within the scope of about 1:1.6 to about 1:2.4, preferably about 1:1.8 to about 1:2.2, more preferably about 1:2. In complex of GH and zinc of the present invention, as though it is preferred that all of GH and zinc contained at molar ratio of about 1:1.6 to about 1:2.4 is in the form of a present complex, GH and/or zinc which do not form a complex may be present.

The pH of the aqueous solution resulting from the above mixing must be such that the bioactivity of GH is not affected, and such that each solubility of GH and zinc salt is not lowered in excess. Although the mixing procedure is normally conducted in distilled water, it may be conducted in water adjusted to be weakly acidic, neutral, or weakly alkaline pH (pH 6 to 9) as necessary. The concentration of GH and water-soluble zinc salt in the water may range within each solubility.

The thus-obtained complex of GH and zinc in water is substantially water-soluble since no precipitate is visibly found in the water. A substantially water-soluble complex of GH and zinc means that the solubility of the complex in 1 ml of water (pH 6 to 8) at normal temperature is more than about 2 mg.

This complex of GH and zinc in water is used for producing a pharmaceutical composition, preferably a sustained-release preparation after being vacuum dried or lyophylized and micronized.

The obtained powder of the complex of GH and zinc is fine-grained and is easier to handle than bulky powder of GH free from zinc, and is very useful for producing a sustained-release preparation on a large scale. For example, a complex of GH and zinc can be obtained as a powder with a mean particle diameter of less than about 10 $\mu$m, preferably about 4 to about 7 $\mu$m.

In the case where the complex is dispersed into an organic solvent containing hereinafter-mentioned biodegradable polymer, particles having a small diameter are very useful for obtaining an enhanced entrapment ratio of GH and an improved release. For example, an entrapment ratio of GH in the sustained-release preparation is preferably more than about 90% and with regard to the a sustained-release of GH, an initial burst ratio of GH is preferable less than about 50%.

The content of the complex of GH and zinc in the sustained-release preparation of the present invention is normally about 0.1% (W/W) to about 40% (W/W), preferably about 1% (W/W) to about 20% (W/W).

The biodegradable polymer is exemplified by high-molecular polymers being slightly soluble or insoluble in water, such as aliphatic polyesters (e.g., homopolymers, copolymers or mixtures thereof synthesized from one or more α-hydroxycarboxylic acids such as glycolic acid, lactic acid, hydroxybutyric acid etc.), hydroxydicarboxylic acids such as malic acid etc., hydroxytricarboxylic acids such as citric acid etc. and others, poly-α-cyanoacrylic acid esters, polyamino acids such as poly-γ-benzyl-L-glutamic acid and so on. These may be used in mixture at appropriate ratios. The type of polymerization may be random, block or graft.

The biodegradable polymer is preferably an aliphatic polyester (e.g., a homopolymer, copolymer or mixture thereof synthesized from one or more α-hydroxycarboxylic acids such as glycolic acid, lactic acid, hydroxybutyric acid etc., hydroxydicarboxylic acids such as malic acid etc., hydroxytricarboxylic acids such as citric acid etc. and others).

Among the above-mentioned aliphatic polyesters, homopolymers or copolymers synthesized from one or more α-hydroxycarboxylic acids (e.g., glycolic acid, lactic acid, hydroxybutyric acid etc.) are preferred from the viewpoint of reliable biodegradability and biocompatibility. More preferably, the aliphatic polyester is a copolymer synthesized from one or more α-hydroxycarboxylic acids (e.g., glycolic acid, lactic acid, hydroxybutyric acid etc.). Also, these copolymers may be used in mixture.

Although the above-described α-hydroxycarboxylic acid may be of the D-, L- or D,L-configuration, it is preferable that the ratio of the D-/L-configuration (mole %) falls within the range from about 75/25 to about 25/75. The ratio of the D-/L-configuration (mole %) is more preferably about 60/40 to about 30/70.

Examples of copolymers of the above-described α-hydroxy-carboxylic acid include copolymers of glycolic acid with another α-hydroxy acid, which is preferably lactic acid, 2-hydroxybutyric acid etc.

The α-hydroxycarboxylic acid copolymer is preferably a lactic acid-glycolic acid copolymer, a 2-hydroxybutyric acid-glycolic acid copolymer etc., more preferably, the α-hydroxycarboxylic acid copolymer is a lactic acid-glycolic acid copolymer etc.

With respect to the lactic acid-glycolic acid copolymer (hereinafter generally called lactic acid-glycolic acid polymer or PLGA), it is preferable that the content ratio (lactic acid/glycolic acid ratio, hereinafter called L/G) (mole/mole %) be about 100/0 to about 40/60. The content ratio is more preferably about 90/10 to about 45/55, and more preferably about 80/20 to about 45/55. The weight-average molecular weight of the lactic acid-glycolic acid copolymer is about 3,000 to about 20,000, preferably about 3,000 to about 16,000 more preferably about 3,000 to about 14,000.

Also, the degree of dispersion of the lactic acid-glycolic acid copolymer (weight-average molecular weight/number-average molecular weight) is preferably about 1.2 to about 4.0, more preferably about 1.5 to about 3.5.

The lactic acid-glycolic acid copolymer can be synthesized by a known process, such as the method described in Japanese Patent Unexamined Publication No. 28521/1986. It is preferable that the copolymer be synthesized by catalyst-free dehydration polymerization condensation.

With respect to the 2-hydroxybutyric acid-glycolic acid copolymer, it is preferable that glycolic acid accounts for about 10 to about 75 mole % and 2-hydroxybutyric acid for the remaining portion. More preferably, glycolic acid accounts for about 20 to about 75 mole %, and still more preferably about 30 to about 70 mole %. The weight-average molecular weight of the 2-hydroxybutyric acid-glycolic acid copolymer is preferably about 2,000 to about 20,000. The degree of dispersion of the 2-hydroxybutyric acid-glycolic acid copolymer (weight-average molecular weight/number-average molecular weight) is preferably about 1.2 to about 4.0, more preferably about 1.5 to about 3.5. A 2-hydroxybutyric acid-glycolic acid copolymer can be synthesized by a known process, such as that described in Japanese Patent Unexamined Publication Nos. 28521/1986 and 112465/1993. It is preferable that the copolymer be synthesized by catalyst-free dehydration polymerization condensation.

Preferable example homopolymers of the above-described α-hydroxycarboxylic acid include homopolymer of lactic acid. The weight-average molecular weight of the homopolymer of lactic acid is about 3,000 to about 20,000, preferably about 3,000 to about 14,000.

A homopolymer of lactic acid can be synthesized by a known process, such as that described in Japanese Patent Unexamined Publication No. 28521/1986. It is preferable that the homopolymer be synthesized by catalyst-free dehydration polymerization condensation.

The above-described 2-hydroxybutyric acid-glycolic acid copolymer may be used in a mixture with polylactic acid. Although the polylactic acid may be of the D- or L-configuration or a mixture thereof, it is preferable that the ratio of the D-/L-configuration (mole %) fall within the range from about 75/25 to about 20/80. The ratio of the D-/L-configuration (mole %) is more preferably about 60/40 to about 25/75, and still more preferably about 55/45 to about 25/75. The weight-average molecular weight of polylactic acid is preferably about 1,500 to about 20,000, more preferably about 1,500 to about 10,000. Also, the degree of dispersion of the polylactic acid is preferably about 1.2 to about 4.0, more preferably about 1.5 to about 3.5.

For producing polylactic acid, two methods are known: ring-opening polymerization of lactide, a dimer of lactic acid, and dehydration polymerization condensation of lactic acid. For obtaining a polylactic acid of relatively low molecular weight for the present invention, direct dehydration polymerization condensation of lactic acid is preferred. This method is, for example, described in Japanese Patent Unexamined Publication No. 28521/1986.

When a 2-hydroxybutyric acid-glycolic acid copolymer and polylactic acid are used in mixture, their mixing ratio is about 10/90 to about 90/10 (% by weight). The mixing ratio is preferably about 20/80 to about 80/20, and more preferably about 30/70 to about 70/30.

In the present specification, weight-average molecular weight is defined as the molecular weight obtained by gel permeation chromatography (GPC) with 9 polystyrenes as reference substances with respective weight-average molecular weights of 120,000, 52,000, 22,000, 9,200, 5,050, 2,950, 1,050, 580 and 162. Number-average molecular weight based on GPC measurement is also calculated. The degree of dispersion is calculated from the weight-average molecular weight and the number-average molecular weight. Measurements are taken using a GPC column KF804L×2 (produced by Showa Denko) and an RI monitor L-3300 (produced by Hitachi, Ltd.) with chloroform as the mobile phase.

The above-described copolymer synthesized by catalyst-free dehydration polymerization condensation, usually has a terminal carboxyl group.

In the present invention, the biodegradable polymer preferably has a terminal carboxyl group.

A biodegradable polymer having a terminal carboxyl group is a polymer in which the number-average molecular weight by GPC determination and that by terminal group determination almost agree.

By terminal group quantitation, number-average molecular weight is calculated as follows:

About 1 to 3 g of the biodegradable polymer is dissolved in a mixed solvent of acetone (25 ml) and methanol (5 ml), and the solution is quickly titrated with a 0.05 N alcoholic solution of potassium hydroxide while being stirred at room temperature with phenolphthalein as an indicator to determine the terminal carboxyl group content; the number-average molecular weight based on terminal group quantitation is calculated using the following equation: Number-average molecular weight based on terminal group quantitation=20,000 A/B A: Weight mass (g) of the biodegradable polymer
B: Amount (ml) of the 0.05 N alcoholic solution of potassium hydroxide added until the titration end point is reached.

For example, in the case of a polymer having a terminal carboxyl group synthesized from one or more α-hydroxy acids by catalyst-free dehydration polymerization condensation, the number-average molecular weight based on GPC measurement and the number-average molecular weight based on terminal group quantitation almost agree. On the other hand, in the case of a polymer having essentially no terminal carboxyl group synthesized from a cyclic dimer by ring-opening polymerization using a catalyst, the number-average molecular weight based on terminal group quantitation is significantly higher than the number-average molecular weight based on GPC determination. This difference makes it possible to clearly differentiate a polymer having a terminal carboxyl group from a polymer having no terminal carboxyl group.

While the number-average molecular weight based on terminal group quantitation is an absolute value, the number-average molecular weight based on GPC determination is a relative value that varies depending on various analytical conditions (e.g., kind of mobile phase, kind of column, reference substance, slice width chosen, baseline chosen etc.); it is therefore difficult to have an absolute numerical representation of the latter. However, the fact that the number-average molecular weight based on GPC determination almost agrees with the number-average molecular weight based on terminal group quantitation means that the number-average molecular weight based on terminal group quantitation falls within the range from about 0.5 to about 2 times, preferably from about 0.8 to about 1.5 times as high as the number-average molecular weight based on GPC determination. Also, the fact that the number-average molecular weight based on terminal group quantitation is significantly higher than the number-average molecular weight based on GPC determination means that the number-average molecular weight based on terminal group quantitation is about 2 times or more as high as the number-average molecular weight based on GPC determination.

As the biodegradable polymer of the present invention, a metal salt (also referred to as a complex) of the above-described biodegradable polymer is preferably used. For instance, a polyvalent metal salt of each kind of biodegradable polymer disclosed in WO 97/01331, preferably a divalent metal salt, especially a zinc salt of lactic acid-glycolic acid copolymer, is preferably used. Biodegradable polymers can be produced by a process described in WO 97/01331 and modifications thereof.

When the polyvalent metal salt of the biodegradable polymer is zinc, the polymer may be produced by reacting the biodegradable polymer with zinc oxide in an organic solvent.

In said process, the biodegradable polymer and zinc oxide are first allowed to exist together in an organic solvent to prepare a solution of a complex of a biodegradable polymer and zinc oxide in the organic solvent. Although the concentration of the biodegradable polymer in the solution varies depending on the molecular weight and the type of the organic solvent, it is, for instance, about 0.1 to about 80%(W/W), preferably about 1 to about 70%(W/W) and more preferably about 2 to about 60%(W/W). Although the amount of zinc oxide added varies depending on the type of the organic solvent, it is, for instance, about 0.001 to about 2%(W/W), preferably about 0.01 to about 1.5%(W/W) and more preferably about 0.1 to about 1%(W/W), based on the amount of the biodegradable polymer.

Regarding the order of addition of the biodegradable polymer and zinc oxide to the organic solvent, zinc oxide both in a powder state or in a dispersed state in the organic solvent can be added to a solution of the biodegradable polymer in the organic solvent, conversely, a solution of the biodegradable polymer in the organic solvent can be added to a dispersion of zinc oxide in the organic solvent. Furthermore, the organic solvent can be added after the biodegradable polymer and zinc oxide both in a powder state have been admixed.

The conditions required to produce a solution of a complex of a biodegradable polymer and zinc oxide, such as complex of PLGA and zinc oxide, from a biodegradable polymer and zinc oxide can be changed according to the type of biodegradable polymer used, the particle diameter of zinc oxide, the type of organic solvent, and these composition ratio. When PLGA is, for example, employed as a polymer, the complex of PLGA and zinc oxide can be obtained by the above reaction usually at about 0 to about 30° C., preferably about 2 to about 25° C., for about 1 to about 168 hours, preferably about 12 to about 96 hours, more preferably about 24 to about 72 hours. The production of a complex of PLGA and zinc oxide in the present invention can be confirmed visibly since zinc oxide which is in a dispersed state at the time of addition dissolves in the organic solvent to give a clear solution. The reaction time is not limited to the above ranges and can be determined using turbidity as an index.

Although this reaction proceeds simply by the co-presence of PLGA and zinc oxide in the organic solvent, the reaction carried out under stirring or shaking advantageously reduces the reaction time. Furthermore, the reaction carried out under ultrasonication is equally preferred. As the reaction temperature becomes higher, the reaction time becomes shorter.

The thus obtained complex of biodegradable polymer and zinc oxide is applied to the next process, preferably as a solution in an organic solvent, or if necessary as a solid after removal of the organic solvent.

The sustained-release preparation of the present invention is produced by removing the organic solvent from dispersion, preferably a solid-in-oil dispersion in which a GH and zinc containing complex at molar ratio of about 1:1.6 to about 1:2.4, preferably as a powder, is dispersed into a solution of a biodegradable polymer (hereafter also means "biodegradable polymer" including a metal salt of the biodegradable polymer) in an organic solvent (oil phase). Methods of producing a sustained-release preparation include the in-water drying method, phase separation method, spray drying method, and modifications thereof.

Methods of producing a sustained-release preparation, e.g., microcapsules, are described below.

(a) In-water Drying Method (S/O/W Method)

In this method, a solution of a biodegradable polymer in an organic solvent is first prepared. The organic solvent used to produce the sustained-release preparation of the present invention preferably has a boiling point not higher than 120° C. Such organic solvents include halogenated hydrocarbons (e.g., dichloromethane, chloro-form, carbon tetrachloride etc.), alcohols (e.g., ethanol, methanol), acetonitrile and so on. These may be used as a mixture at appropriate ratios. The organic solvent is preferably dichloromethane and acetonitrile, and still more preferably dichloromethane. The concentration of the biodegradable polymer in the organic solvent solution is normally about 0.01 to about 80% (W/W), preferably about 0.1 to about 70% (W/W), and more preferably about 1 to about 60% (W/W), depending on the molecular weight of the biodegradable polymer, kinds of organic solvent and so on.

To the organic solvent solution (oil phase) of the biodegradable polymer thus obtained, a complex of GH and zinc is added or dispersed. In this operation, the amount of complex of GH and zinc added is set so that the complex of GH and zinc weight ratio to biodegradable polymer is up to about 0.4, preferably about 0.2. As a method of dispersing, a powder a of complex of GH and zinc may be added and dispersed uniformly, and the lyophilized bulk of complex of GH and zinc is added directly and dispersed uniformly by atomizing and mixing in an oil phase.

The organic solvent suspension (S/O type dispersion) thus prepared is added to an aqueous phase(water phase) to form an S/O/W type emulsion using a turbine type mechanical stirrer, ultrasonic equipment or the like, followed by evaporation of the solvent in the oil phase, to yield microcapsules. The volume of the aqueous phase is normally chosen over the range of about 1 to about 10,000 times, preferably about 5 to about 2,000 times, and more preferably about 10 to about 1,000 times, the volume of the oil phase.

An emulsifier may be added to the external aqueous phase. The emulsifier may be any one, as long as it is capable of forming a stable S/O/W type emulsion. Examples of such emulsifiers include anionic surfactants, nonionic surfactants, polyoxyethylene castor oil derivatives, polyvinylpyrrolidone, polyvinyl alcohol, carboxymethyl cellulose, lecithin, gelatin, hyaluronic acid and so on. These may be used in combination as appropriate. The emulsifier concentration in the external aqueous phase is preferably about 0.001 to about 20% (W/V), more preferably about 0.01 to about 10% (W/V), and still more preferably about 0.05 to about 5% (W/V).

The thus obtained microcapsules are recovered by centrifugation or filtration, washed with distilled water to remove the emulsifier etc. adhering to the surface of microcapsules, redispersed in distilled water, and lyophilized. Then, if necessary, water and the organic solvent in the microcapsules are further removed by heating. The heating may be conducted under reduced pressure. Regarding the heating conditions, heating and drying are conducted at a temperature not lower than a glass transition temperature of the biodegradable polymer and not so high as to cause aggregation of each microcapsule particle. The heating and drying are conducted preferably at a temperature ranging from the glass transition temperature of the biodegradable polymer to a temperature which is about 30° C. higher than the glass transition point obtained using a differential scanning calorimeter when the temperature is increased at a rate of about 10 to about 20° C. per minute.

(b) Phase Separation Method (Coacervation Method)

In this method, a coacervating agent is gradually added to the above described S/O type dispersion under stirring to precipitate and solidify microcapsules. The amount of the coacervating agent used is about 0.01 to about 1,000 times by volume, preferably about 0.05 to about 500 times by volume, especially preferably about 0.1 to about 200 times by volume. Any coacervating agent can be used, as long as it is a polymeric, mineral oil or vegetable oil compound miscible with the organic solvent for dissolution of a biodegradable polymer and it does not dissolve the biodegradable polymer used. Specifically, examples of such coacervating agents include silicone oil, sesame oil, soybean oil, corn oil, cottonseed oil, coconut oil, linseed oil, mineral oil, n-hexane and n-heptane. Two or more of these may be used in combination. The thus obtained microcapsule are recovered by filtration, and washed repeatedly with heptane etc. to remove the coacervating agent. Further, washing is conducted in the same manner as in the above (a), followed by lyophilization.

(c) Spray-drying Method

In this method, the above described S/O type dispersion is sprayed via a nozzle into the drying chamber of a spray drier to volatilize the organic solvent in fine droplets in a very short time to yield microcapsules. Examples of the nozzle include, for instance, a two-fluid nozzle type, a pressure nozzle type and a rotary disc type. It is also advantageous, if necessary, to spray an aqueous solution of the above-described antiaggregation agent via another nozzle in order to prevent aggregation of each microcapsule particle. The thus obtained microcapsule is washed in the same manner as in the above (a), if necessary followed by heating (if necessary under reduced pressure) to remove water and the organic solvent.

The sustained-release preparation of the present invention is preferably used in the form of fine particles. This is so that the sustained-release preparation does not cause undue pain to the patient when administered via an injection needle for ordinary subcutaneous or intramuscular injection. The mean particle diameter of the sustained-release preparation, for example, is about 0.1 to about 300 $\mu$m, preferably about 1 to about 150 $\mu$m, and more preferably about 2 to about 100 $\mu$m.

In the present invention, the microcapsule may be fine particles (called microspheres) comprising the active ingredient (complex of GH and zinc) and a base for the microcapsule (biodegradable polymer). Typically, they include microcapsules containing one core of active ingredient in one particle, or microcapsules containing many cores of active ingredient in one particle.

The sustained-release preparation of the present invention, for example, can be administered as microcapsules, in the form of various dosage forms of non-oral preparations (e.g., intramuscular, subcutaneous or visceral injections or indwellable preparations, nasal, rectal or uterine transmucosal preparations etc.) or oral preparations (e.g., capsules such as hard capsules, soft capsules etc., solid preparations such as granules and powders etc., liquid preparations such as suspensions etc.).

In the present invention, the sustained-release preparation is preferably used for injection. When the sustained-release preparation is a microcapsule, for instance, it can be prepared as an aqueous suspension by suspending microcapsules in water, along with a dispersing agent (e.g., surfactants such as polysorbate (Tween 80, Bio Rad) and HCO-60 (Nikko Chemicals), polysaccharides such as carboxymethyl cellulose, sodium alginate and sodium hyaluronate etc.), a preservative (e.g., methyl paraben, propyl paraben etc.), an isotonizing agent (e.g., sodium chloride, mannitol, sorbitol, glucose etc.), etc., to yield a sustained-release preparation for injection of practical use. Alternatively, the sustained-release preparation of the present invention is prepared as an oily suspension by dispersing microcapsules, along with a vegetable oil such as sesame oil or corn oil with or without a phospholipid such as lecithin, or a medium-chain fatty acid triglyceride (e.g., MIGLYOL 812, Huls A. G. (Marl, Germany)), to yield a sustained-release preparation for injection of practical use.

When the sustained-release preparation is a microcapsule, for instance, its mean particle size is chosen over the range from about 0.1 to about 300 μm as long as the requirements concerning degree of dispersion and needle passage are met, when it is to be used as an injectable suspension. Preferably, the particle size falls within the range from about 1 to about 150 μm, more preferably about 2 to about 100 μm.

The above-described microcapsule can be prepared as a sterile preparation, without limitation, for example, by the method in which the entire production process is sterile, the method in which gamma rays are used as sterilant, and the method in which an antiseptic is added.

The sustained-release preparation of the present invention is of low toxicity and can be safely used in mammals (e.g., humans, bovines, swines, dogs, cats, mice, rats, rabbits etc.).

The sustained-release preparation of the present invention is useful for treating or preventing adult GH hyposecretion, Turner's syndrome, pituitary dwarfism, chronic renal diseases, achondroplasia, adult hypopituitarism, Down syndrome, Silver syndrome, hypochondroplasia, juvenile chronic arthritis and static heart diseases etc.

Depending on duration of the release, target disease, subject animal species and other factors, the dose of the sustained-release preparation may be set at any level, as long as the effective concentration of GH in the body is maintained. For instance, when the sustained-release preparation is designed for two weeks release and administered to patients for pituitary dwarfism, the dose of an effective ingredient can be chosen from the range of preferably about 0.01 to about 5 mg/kg body weight, more preferably about 0.03 to about 1 mg/kg body weight, per an adult, administered once every two weeks.

The complex of GH and zinc of the present invention has low toxicity and while the complex of GH and zinc can be administrated as it is, it is usually administered in the form of a composition formulated by conventional methods using pharmaceutically acceptable carriers or diluents for pharmaceutical compositions adequately selected from excipients (e.g. calcium carbonate, kaolin, sodium hydrogencarbonate, lactose, corn starch, crystalline cellulose, talc, fine granulated sugar and porous substance), binders (e.g. dextrin, gum, a-starch, gelatin, hydroxypropyl cellulose, hydroxypropylmethyl cellulose and furran), thickeners (e.g. natural rubbers and cellulose derivatives), disintegrants (e.g. carboxymethyl cellulose calcium, closcarmellose sodium, clospovidone, low-substituted hydroxypropyl cellulose and partial α-starch), solvents (e.g. water for injection, physiological saline, ringels solution, alcohol, propylene glycol, sesame oil and corn oil), dispersing agents (e.g. Tween 80, HCO 60, carboxymethyl cellulose and sodium alginate), suspending agents (e.g. sodium lauryl sulfate and benzalkonium chloride), dissolution acids (e.g. polyethylene glycol, propylene glycol, D-mannitol, benzyl benzoate, ethanol, torisaminomethane, triethanolamine, sodium carbonate and sodium citrate), anesthetizing agents (e.g. benzylalcohol), buffers (e.g. phosphate, acetate, carbonate and citrate), lubricants (e.g. magnesium stearate, calcium stearate, talc, starch and sodium benzoate), colorants (e.g. tar pigment, caramel, iron sesquioxide, titanium oxide and riboflavins), falvoring agents (e.g. sweeteners and perfume), stabilizers (e.g. sodium sulfite and ascorbic acid) and preservatives (e.g. parabens and sorbic acid) in adequate amounts respectively. The pharmaceutical composition of the present invention which may contain the above-mentioned carriers or diluents for pharmaceutical compositions contains an effective amount of the complex of GH and zinc for preventing and treating the above-diseases in a similar way to the above-sustained-release preparation. The content of the complex of GH and zinc of the present invention in the pharmaceutical composition ranges usually from about 0.1 to about 100 weight % relative to the whole weight of the pharmaceutical composition.

Although the sustained-release preparation may be stored at normal temperature or in a cold place, it is preferable to store it in a cold place. Normal temperature and a cold place as mentioned herein are as defined by the Pharmacopoeia of Japan, specifically, 15 to 25° C. for normal temperatures and under 15° C. for cold places.

EXAMPLES

The present invention will be explained in more detail by the following Examples, Reference Examples, Comparative Examples and Experimental Examples. The scope of the present invention is not intended to be restricted by said examples. In the present specification and Examples, amino acid abbreviations are based on those recommended by the IUPAC-IUB Commission on Biochemical Nomenclature, or those used commonly in the related field, and as shown below. In the case that amino acids have optical isomers, they represent L-type unless otherwise specified.

SDS: Sodium dodecylsulfate
Gly: Glycine
Ala: Alanine
Val: Valine
Leu: Leucine
Ile: Isoleucine
Ser: Serine
Thr: Threonine
Cys: Cystein
Met: Methionine
Glu: Glutamic acid
Gln: Glutamine
Asp: Aspartic acid
Asn: Asparagine
Lys: Lysine
Arg: Arginine
His: Histidine
Phe: Phenylalanine
Tyr: Tyrosine
Trp: Tryptophan
Pro: Proline
Asx: Asp+Asn
Glx: Glu+Gln Reference Example 1

Construction of Expression Vector for GH Using T7 Promoter

The structure gene of GH was isolated as about 0.75 kb of EcoRI-EcoRV fragment from plasmid pHGH107 (ATCC 31538 or ATCC 40011) described in Japanese Patent Publication No. 12996/1994. On the other hand, T7 promoter and ampicillin resistant gene were isolated as about 4.6 kb of NdeI-BamHI fragment from pET-3C [Rosenberg et al., Gene, 56, 125 (1987)]. Both of the two fragments were treated with T4 DNA polymerase (DNA blunting kit; Takara Shuzo, Inc.) and ligated with T4 DNA ligase, followed by introduction into *Escherichia coli* JM109 and selection of ampicillin resistant transformant. From the obtained 12 colonies, plasmids were prepared and digested with PstI. As a result, it was found that GH gene was inserted in a correct direction in the plasmids from the 6 colonies. The plasmid obtained from one transformant among the 6 colonies was named as pTGA201.

Reference Example 2

Expression of Met-GH in *Escherichia coli*

*Escherichia coli* JM109 was transformed with λ phage (Studie, Supura) having RNA polymerase gene of T7 phage. Thereafter, into the obtained *Escherichia coli* JM109 (DE3), GH expression vector pTGA201 obtained in Reference Example 1 was introduced to obtain *Escherichia coli* JM109 (DE3)/pTGA201.

*Escherichia coli* JM109 (DE3)/pTGA201 was inoculated into a flask of 2 liter capacity containing 1 liter of LB medium [1% peptone, 0.5% yeast extract, 0.5% sodium chloride] and 50 µg/ml ampicillin and then subjected to rotary shaking cultivation at 30° C. for 16 hours. The resultant culture liquid was then transferred to a 50 liter jar fermentor containing 20 liter of LB medium [0.02% antiforming agent (New Pole LB-625; San-yo Kasei Kogyo), 50 µg/ml ampicillin], after which it was subjected to cultivation under aeration and agitation at 37° C. for 6 hours. The resultant culture liquid was then transferred to a 500 liter jar fermentor containing 360 liter of a liquid production medium [1.68% sodium hydrogen phosphate, 0.3% potassium dihydrogen phosphate, 0.1% ammonium chloride, 0.05% sodium chloride, 0.024% magnesium sulfate, 0.02% antiforming agent (New Pole LB-625), 0.0005% thiamine hydrochloride, 1.5% glucose, 1.5% casamino acid], after which it was subjected to cultivation under aeration and agitation at 37° C. When the Klett value was about 500, 5.95 mg/L/minute of isopropyl-β-D-thiogalactopyronoside (IPTG) was added to the medium and the cultivation was further continued for 4 hours. The culture liquid was centrifuged to obtain about 4.5 kg of wet cells which were frozen at −80° C.

The above-described transformant *Escherichia coli* JM109 (DE3)/pTGA201 has been deposited FERM BP-5632 at the NIBH (National Institute of Bioscience and Human-Technology) and IFO 16001 at the IFO (Institute Fermentation Osaka).

Reference Example 3

Activation of Met-GH

Two kg of wet cells obtained in Reference Example 2 was dissolved in 6 l of 50 mM Tris-HCl and guanidine hydrochloride (pH 8.0), followed by centrifugation (10000 rpm, 120 minutes). To 6 liters of the resultant supernatant, was added 18 liter of a solution (pH 8.0) containing 50 mM Tris-HCl, 0.28 mM GSSG and 0.7 M Arg to adjust pH 8.0, followed by standing at 4° C. for 5 days to continue activation of Met-GH.

Reference Example 4

Purification of Met-GH

The solution obtained in Reference Example 3 was subjected to salting-out and concentration by Pellicon cassette system (PTGC membrane; Millipore Corporation) and with adding a solution (pH 8.0) of 20 mM Tris-HCl and 2.5 M urea until electric conduction became not more than 10 mS. The obtained concentrate was centrifuged (10000 rpm, 60 minutes) to obtain 5 liter of supernatant. The supernatant was loaded on DEAE-Toyopearl 650M column (20 cm φ×84 cm, Tosoh) equilibrated with a solution (pH 8.0) of 20 mM Tris-HCl and 2.5 M urea, followed by adsorption and washing. The column was eluted with using a linear concentration gradient consisting of 0–25% solution B (B=20 mM Tris-HCl, 2.5 M urea, 1M NaCl, pH 8.0) at 300 ml/minute of flow rate for 100 minutes. The eluted solution containing Met-GH of 10 liter was again subjected to salting-out and concentration by Pellicon cassette system (PTGC membrane; Millipore). The concentrated solution was passed through DEAE-5PW column (21 cm φ×30 cm, Tosoh) using HPLC method (Gilson HPLC system; Gilson). The column was eluted using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at 320 ml/minute of flow rate for 70 minutes. To the obtained Met-GH fraction 6 liter, was added 2 M Tris-HCl (pH 7.8) to adjust to pH 7.2, followed by salting-out and concentration by Pellicon cassette system (PTGC membrane; Millipore) to obtain 9,979 mg of Met-GH.

Reference Example 5

Removal of N-terminal Met

To 1650 ml solution of Met-GH obtained in Reference Example 4, was added 413 ml of a solution containing 35 mM copper sulfate, 2.5 M glyoxylic acid and 6 M pyridine and the mixture was stirred and allowed to stand at 25° C. for 1 hour. The reaction solution was passed at a flow rate of 3 liter/h through Sephadex G-25 column (11.3 cm φ×125 cm, Pharmacia) equilibrated with a solution (pH 8.0) of 20 mM Tris-HCl and 2.5 M urea and the column was washed with the same solution to collect the fraction of diketone derivative of Met-GH. The eluted fraction was directly added to a 4 liter solution of 4M acetic acid, 4 M sodium acetate, 80 mM o-phenylenediamine and 3 M urea with stirring. After the elution, the reaction solution (8 liters) was allowed to stand at 4° C. for 3 days. The solution was subjected to salting-out by Pellicon cassette system (PTGC membrane; Millipore). The concentrated solution (4 liters) was passed at a flow rate of 3 liter/h through Sephadex G-25 column (11.3 cm φ×140 cm, Pharmacia) equilibrated with a solution (pH 8.0) of 20 mM Tris-HCl and 2.5 M urea to collect the fraction of GH (4.7 liter). The obtained fraction was passed through a DEAE-5PW column (21 cm φ×30 cm, Tosoh) using HPLC method (Gilson HPLC system; Gilson). The column was eluted using a pH gradient consisting of 70–85% solution B (A=50 mM Tris-HCl and 2.5 M urea (pH 8.0); B=50 mM MES [2-(N-morpholino)ethane sulfonate] and 2.5 M urea (pH 4.0)) at a flow rate of 320 ml/minute for 70 minutes to collect 10 liter fraction of GH. To the obtained GH fraction was added 500 ml solution of 2 M Tris-HCl (pH 7.8) to adjust to pH 7.2, followed by concentration with Minitan II (PTGC membrane; Millipore). The concentrated solution 500 ml was passed at a flow rate of 2 liter/h through Sephacryl S-100 column (11.3 cm φ×50 cm, Pharmacia) equilibrated with distilled water to collect the GH fraction 1651 ml, and followed by filtration with Millipack 60 (Millipore) to obtain GH solution 1487 ml (3309 mg of GH).

Reference Example 6

Determination of Feature of GH (a) Analysis with SDS-Polyacrylamide Gel Electrophoresis To the GH solution obtained in Reference Example 5 was added the same volume of Sample buffer [Laemmli, Nature, 227, 680 (1970)] containing 100 mM DTT, and the mixture was heated at 95° C. for 2 minutes, followed by electrophoresis with Multi Gel 10/20 (Daiichi Pure Chemicals). After electrophoresis, the gel was stained with Coomassie brilliant blue and only one single band at about 22 kd of the purified protein was obtained.

(b) Analysis of Amino Acid Composition

Analysis of amino acid was used for the determination of amino acid composition was done with an amino acid analyzer (L-8500A, Hitachi). The amino acid composition of GH obtained agreed with that predicted from cDNA sequence of GH (Table 1).

TABLE 1

Analysis of amino acid composition

| Amino acid | Number of residues per 1 mole | Values predicted from cDNA sequence of GH |
|---|---|---|
| Asx | 20.2 | 20 |
| Thr[1] | 10.0 | 10 |
| Ser[1] | 16.7 | 18 |
| Glx | 27.0 | 27 |
| Pro | 8.1 | 8 |
| Gly | 8.2 | 8 |
| Ala | 7.6 | 7 |
| Cys[2] | N.D. | 4 |
| Val | 7.0 | 7 |
| Met | 3.0 | 3 |
| Ile | 7.7 | 8 |
| Leu | 27.9 | 26 |
| Tyr | 8.1 | 8 |
| Phe | 12.7 | 13 |
| His | 3.2 | 3 |
| Lys | 8.9 | 9 |
| Arg | 10.9 | 11 |
| Trp | 0.8 | 1 |

Acid hydrolysis (6N HCl, 4% thioglycolic acid, 110° C., Mean value of those obtained after 24 and 48 hours of hydrolysis)
[1]Value extrapolated on the assumption that hydrolysis time was 0 hours.
[2]Undetected
Analysis was carried out using about 20 μg of GH.

(c) Analysis of N-terminal Amino Acid Sequence

The N-terminal amino acid sequence of GH was determined using a gas-phase protein sequencer (Applied Biosystems, 477A model). The N-terminal amino acid sequence of GH obtained agreed with that predicted from cDNA sequence of GH (Table 2).

TABLE 2

Analysis of N-terminal amino acid sequence

| Residue No. | PTH[1]-amino acid detected (pmol) | amino acid predicted from cDNA sequence of GH |
|---|---|---|
| 1 | Phe (949) | Phe |
| 2 | Pro (404) | Pro |
| 3 | Thr (422) | Thr |
| 4 | Ile (744) | Ile |
| 5 | Pro (283) | Pro |
| 6 | Leu (514) | Leu |
| 7 | Ser (136) | Ser |
| 8 | Arg (36) | Arg |
| 9 | Leu (377) | Leu |
| 10 | Phe (408) | Phe |
| 11 | Asp (77) | Asp |
| 12 | Asn (230) | Asn |
| 13 | Ala (435) | Ala |
| 14 | Met (334) | Met |
| 15 | Leu (398) | Leu |
| 16 | Arg (67) | Arg |
| 17 | Ala (488) | Ala |
| 18 | His (30) | His |

TABLE 2-continued

Analysis of N-terminal amino acid sequence

| Residue No. | PTH[1]-amino acid detected (pmol) | amino acid predicted from cDNA sequence of GH |
|---|---|---|
| 19 | Arg (42) | Arg |
| 20 | Leu (406) | Leu |

[1]phenylthiohydantoin
Analysis was carried out using 1 nmol of GH.

(d) Analysis of C-terminal Amino Acid

Analysis of C-terminal amino acid was done by determination of C-terminal amino acid with amino acid analyzer (L-8500A, Hitachi). The C-terminal amino acid of GH obtained agreed with that predicted from cDNA sequence of GH (Table 3).

TABLE 3

Analysis of C-terminal amino acid

| C-terminal amino acid | Yield (%) |
|---|---|
| Phe | 52 |

Vapor-phase hydrazinolysis (100° C., 3.5 hours)
Analysis was carried out using 18 nmol of GH.

(e) Determination of GH Activity

GH purified and obtained in Reference Example 5 had a cell growth enhancing activity to Nb 2 cells according to the method described in Journal of Clinical Endocrinology and Metabolism, 51, 1058 (1980) almost similar to a standard product (Chemicon International, USA).

Example 1

(1) Production of Complex of GH and Zinc

To 120 ml of aqueous solution of genetic recombinant type GH (2 mg/ml) obtained according to Reference Example 5, 0.5 ml of two kinds of aqueous solution of zinc acetate whose concentration was set so that the molar ratio of zinc to 1 mole of GH was 1.8 and 2.0, were added independently and were lyophilized to yield complex of GH and zinc (about 230 mg).

(2) Production of Microcapsule Containing GH 1.89 g of lactic-glycolic acid copolymer (lactic acid/glycolic acid=50/50, average molecular weight converted into polystyrene=12,000, viscosity=0.145 dl/g) was dissolved in 4 ml of dichloromethane, and after 10 mg of zinc oxide was added, it was stirred (60 rpm) at 25° C. to be dissolved completely. To this solution of polymer in an organic solution, 100 mg of complex of GH and zinc obtained in the above (1) was added and was atomized by Polytron(Kinematica). The obtained S/O dispersion was added to 800 ml of 0.1% aqueous solution of polyvinyl alcohol, and stirred and emulsified by homomixer. After drying in water for 2 hours, it was washed with distilled water and lyophilized to yield microcapsules containing GH (1.07 g(1:1.8), 0.91 g(1:2.0)).

Comparative Example 1

(1) Production of GH Powder

To 120 ml of aqueous solution of genetic recombinant type GH (2 mg/ml) obtained according to Reference Example 5, 0.5 ml of various kinds of aqueous solution of zinc acetate whose concentration was set so that the molar ratio of zinc to 1 mole of GH were 0, 3.0, 4.0, 5.0 and 6.0, were added independently and was lyophilized to yield GH powder (about 230 mg).

(2) Production of Microcapsule Containing GH

By the same method of Example 1-(2), microcapsule containing GH (0.95 g(1:0), 1.23 g(1:3), 1.13 g(1:4), 1.2 g(1:5), 1.27 g(1:6)) was obtained by using the GH powder described in the above-described (1).

Experimental Example 1

By using microcapsules produced in Example 1-(2) and Comparative Example 1-(2), the following experiments were conducted.

(1) Content of GH

300 $\mu$l of acetonitrile was added to 4 mg of microcapsules produced in Example 1-(2) or Comparative Example 1-(2), the base lactic acid-glycolic acid copolymer was dissolved in it, and 700 $\mu$l of aqueous solution which contained 0.02% bovine serum albumin-0.05% trifluoro acetic acid was added by stirring to elute GH. In the supernatant obtained by the centrifugation, the content of GH in the microcapsule was determinated by high performance liquid chromatography. The result is shown in Table 4.

As illustrated by Table 4, more than 90% entrapment ratio of GH was obtained in the case of using the complex of the present invention which contains GH and zinc at a molar ratio of 1.8 or 2.0 of zinc to 1 mole of GH.

It is clear that the sustained-release preparation containing a complex of GH and zinc in the present invention has an excellent entrapment ratio of GH.

(2) Release In Vivo

Microcapsules produced in Example 1-(2) and Comparative Example 1-(2) were subcutaneously administered to imunosuppressed SD rats (male, 6 weeks old) in the amount of 6 mg GH/rat. Blood was collected periodically and the serum concentration was assayed with radioimuunoassay kit (Ab beads HGH : Eiken Kagaku). Immunosuppressed SD rats were obtained by administering Prograph® (Fujisawa Pharm.) in the amount of 0.4 mg/rat on 3 days before administration of microcapsule and in the amount of 0.2 mg/rat on the administration day and 4, 7, 11 and 14 days after the administration. The amount of GH released on the first day and 1–18 days after the administration of microcapsule were calculated based on pharmaco kinetic parameters (AUC and clearance) obtained by the changes of serum GH concentration. The initial burst amount GH was obtained by ratio of the amount of GH released during the first day after the administration to the amount of GH administered. The result is shown in the Table 4.

As shown in Table 4, in microcapsules containing the complex of GH and zinc at a molar ratio of 1:1.8 or 1:2.0, the initial burst amount of GH (amount released until 1 day (24 hours) after administration) was low (less than about 30%) and the amount of GH release after 1 day (amount released from 1 day after administration (24 hours to 18 days after administration)) was high (more than about 50%). In the microcapsule produced in Comparative Example 1-(2), an effective sustained release was not obtained because the initial burst amount was high and the amount of release after it was low.

It is clear that the sustained-release preparation containing a complex of GH and zinc in the present invention has an excellent sustained-release.

TABLE 4

| microcapsule | GH/zinc molar ratio | entrapment ratio(%) | amount of GH release 1 day | amount of GH release 1–18 days | initial burst ratio (%) |
|---|---|---|---|---|---|
| Example 1 | 1:1.8 | 92 | 1.60 | 2.31 | 26.7 |
|  | 1:2.0 | 92 | 1.23 | 2.68 | 20.5 |
|  | 1:0 | 88 | 3.26 | 1.96 | 54.3 |
| Comparative Example 1 | 1:3.0 | 73 | 4.32 | 1.95 | 72.0 |
|  | 1:4.0 | 75 | 4.83 | 1.97 | 80.5 |
|  | 1:5.0 | 70 | 5.99 | 1.44 | 83.2 |
|  | 1:6.0 | 73 | 4.46 | 1.91 | 74.3 |

Experimental Example 2

To 2 ml of aqueous solution of genetic recombinant type GH (2 mg/ml) obtained according to Reference Example 5, 50 $\mu$l of various kinds of aqueous solution of zinc acetate whose concentration was set so that the molar ratio of zinc to 1 mole of GH were 0, 1.4, 1.6, 1.8, 2.0, 2.2, 2.4, 3.0, 4.0, 5.0 and 6.0, were added independently and lyophilized. The obtained lyophilized powder was dispersed in 2 ml of dichloromethane, atomized and micronized by Vortex mixer. The distribution of particle size was determined by using laser diffraction apparatus of determining distribution of particle size (SALD2000A; Shimazu). The results are shown in FIG. 1. In FIG. 1, particle size(mean particle diameter: $\mu$m) is shown by ●.

As shown by FIG. 1, the complex of GH and zinc at a molar ratio of 1:1.6 to 1:2.4 in the present invention showed the mean particle diameter being less than 5 $\mu$m.

It is clear that the complex of GH and zinc in the present invention is fine particle.

Experimental Example 3

Figure 2:
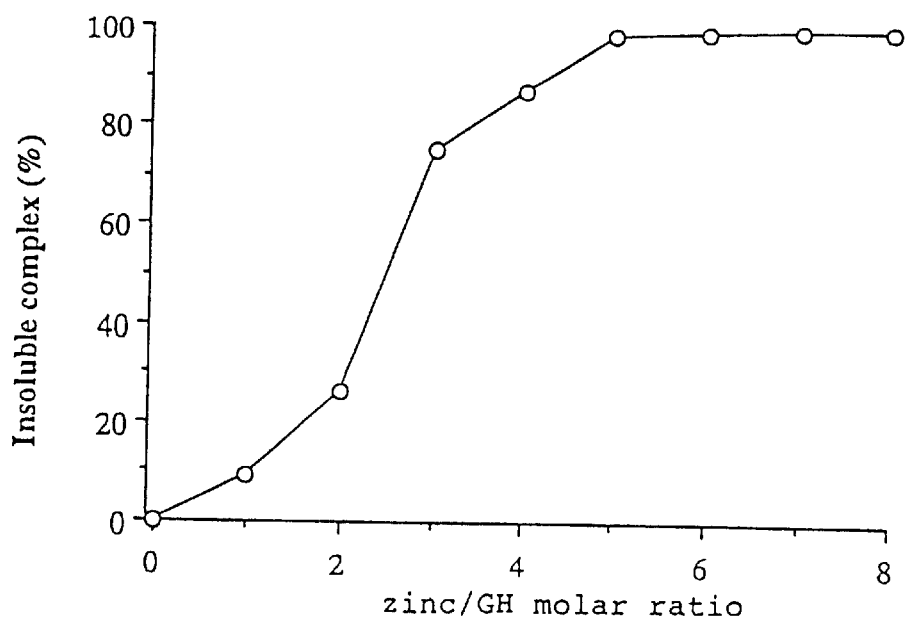
FIG. 2 shows the changes in solubility of a complex according to the changes of the composition ratio of GH and zinc in a complex of GH and zinc.

To 1 ml of aqueous solution of genetic recombinant type GH (2 mg/ml) obtained according to Reference Example 5, 25 $\mu$l of various kinds of aqueous solution of zinc acetate whose concentration was set so that the molar ratio of zinc to 1 mole of GH were 0, 1.0, 2.0, 3.0, 4.0, 5.0, 6.0, 7.0 and 8.0 were added independently, and was centrifugated for 5 minutes at 12,000 rpm/minute. The obtained supernatant was filtered through 0.45 $\mu$m filter and the concentration of GH was quantitatively analyzed by high performance liquid chromatography to calculate the ratio formed of water-insoluble complex (ratio of GH in water-insoluble complex to total amount of GH added (%)). The result is shown in FIG. 2. In FIG. 2, the ratio of water-insoluble complex formed is shown by ○.

As shown by FIG. 2, in the case that the zinc molar ratio to 1 mole of GH is less than 2.0, the co-existing water-insoluble component was less than 30% and the complex was substantially water-soluble.

It is clear that the complex of GH and zinc in the present invention is substantially water-soluble.

What is claimed is:

1. A complex of human growth hormone and zinc, comprising human growth hormone and zinc at a molar ratio of about 1:1.6 to about 1:2.4.

2. A complex of claim 1, wherein the complex has a mean particle diameter of less than 10 $\mu$m.

3. A method for producing a complex of human growth hormone and zinc according to claim 1, which comprises mixing human growth hormone and zinc in the form of a zinc salt at a molar ratio of about 1:1.6 to about 1:2.4, for a time and under conditions to produce the complex.

4. A method for producing a micronized human growth hormone complex, which comprises atomizing a complex of human growth hormone and zinc, said complex comprising human growth hormone and zinc at a molar ratio of about 1:1.6 to about 1:2.4, thereby to produce the micronized human growth hormone complex.

5. A pharmaceutical composition which comprises a complex of claim 1 in admixture with a pharmaceutically acceptable carrier or diluent.

6. A pharmaceutical composition for treating pituitary dwarfism, which comprises an effective amount of the complex of claim 1 in admixture with a pharmaceutically acceptable carrier or diluent.

7. A method according to claim 3, wherein the zinc salt is a water-soluble zinc salt.

* * * * *